US007741371B2

(12) United States Patent
Dalton et al.

(10) Patent No.: US 7,741,371 B2
(45) Date of Patent: Jun. 22, 2010

(54) SELECTIVE ANDROGEN RECEPTOR MODULATORS AND METHODS OF USE THEREOF

(75) Inventors: James T. Dalton, Upper Arlington, OH (US); Duane D. Miller, Germantown, TN (US); Craig A. Marhefka, Belmont, MA (US); Wenqing Gao, Columbus, OH (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 11/394,181

(22) Filed: Mar. 31, 2006

(65) Prior Publication Data
US 2006/0241180 A1    Oct. 26, 2006

Related U.S. Application Data

(63) Continuation-in-part of application No. 10/462,837, filed on Jun. 17, 2003, now Pat. No. 7,022,870.

(60) Provisional application No. 60/388,739, filed on Jun. 17, 2002.

(51) Int. Cl.
*A61K 31/165* (2006.01)
(52) U.S. Cl. .................. 514/619; 514/522; 514/524; 514/616; 514/620
(58) Field of Classification Search ................ 564/154; 558/417; 514/522, 524, 616, 628, 619, 620
See application file for complete search history.

(56) References Cited

U.S. PATENT DOCUMENTS

| 3,875,229 | A | 4/1975 | Gold |
| 4,139,638 | A | 2/1979 | Neri et al. |
| 4,191,775 | A | 3/1980 | Glen |
| 4,239,776 | A | 12/1980 | Glen et al. |
| 4,282,218 | A | 8/1981 | Glen et al. |
| 4,386,080 | A | 5/1983 | Crossley et al. |
| 4,465,507 | A | 8/1984 | Konno et al. |
| 4,636,505 | A | 1/1987 | Tucker |
| 4,880,839 | A | 11/1989 | Tucker |
| 5,162,504 | A | 11/1992 | Horoszewicz |
| 5,609,849 | A | 3/1997 | Kung |
| 5,656,651 | A | 8/1997 | Sovak et al. |
| 6,019,957 | A | 2/2000 | Miller et al. |
| 6,071,957 | A | 6/2000 | Miller et al. |
| 6,160,011 | A | 12/2000 | Miller et al. |
| 6,482,861 | B2 | 11/2002 | Miller et al. |
| 6,492,554 | B2 | 12/2002 | Dalton et al. |
| 6,569,896 | B2 | 5/2003 | Dalton et al. |
| 7,022,870 | B2 * | 4/2006 | Dalton et al. ............... 558/413 |

FOREIGN PATENT DOCUMENTS

| EP | 0040932 | 12/1981 |
| EP | 0100172 | 2/1984 |
| EP | 0002892 | 2/1985 |
| EP | 0253503 | 1/1988 |
| GB | 1360001 | 3/1970 |
| JP | 52-128329 | 10/1977 |
| JP | 54-63047 | 12/1980 |
| WO | WO9519770 | 7/1995 |
| WO | WO9805962 | 2/1998 |
| WO | WO9853826 | 12/1998 |
| WO | WO9855153 | 12/1998 |
| WO | WO0127622 | 4/2001 |
| WO | WO0128990 | 4/2001 |
| WO | WO0134563 | 5/2001 |
| WO | WO0200617 | 1/2002 |
| WO | WO0216310 | 2/2002 |

OTHER PUBLICATIONS

U.S. Appl. No. 10/298,229, filed Nov. 28, 2002, Miller, et al.
U.S. Appl. No. 10/270,232, filed Oct. 15, 2002, Dalton, et al.
U.S. Appl. No. 10/277,108, filed Oct. 23, 2002, Dalton, et al.
U.S. Appl. No. 10/270,233, filed Oct. 15, 2002, Dalton, et al.
U.S. Appl. No. 10/270,732, filed Oct. 15, 2002, Dalton, et al.
U.S. Appl. No. 10/310,150, filed Dec. 5, 2002, Steiner, et al.
Eliason, et al (2002) "High Throughput Fluorescence Polarazation-Based Screening Assays for the Identification of Novel Nuclear Receptor Ligands." Abstracts of Papers, 223rd ACS National Meeting, Orlando, FL, U.S.
Tucker, et al (1988) "Resolution of the Nonsteroidal Antiandrogen—4'-Cyano-3-[(4-flurophenyl) solfonyl1]—2-hydroxy-2 methyl-3'-(trifluromythyl1)—propionanilide and the Determination of the Absolute Configuration of the Active Enantiomer:" J Med Chem 31, 885-887.
Mckillop, et al (1995) "Enantioselective metabolism and pharmacokinetics of Casodex in the male rat" vol. 25, No. 6, 623-634.
Kirkovsky, et al (1997) "[$^{125}$I]-Radionated Bicalutamide Analogs as Potential Imaging Agents for Prostate Cancer" Poster Presentation MEDI 155, 214th ACS National Meeting Las Vegas. NV, Sep. 7-11, 1997, Department of Pharmaceutical Sciences, University of Tennessee, Memphis, TN 38183.
Baird, et al (1993) "Hormonal Contraception—Drug Therapy", The New England Journal of Medicine, 1543-1549.
F.C. W. Wu (1988) "Male Contraception: Current Status and Future Prospects", Clinical Endocrinology , 29, 443-465.
Djerassi, et al "A new look at male contraception", Nature, vol. 370 11-12.

(Continued)

*Primary Examiner*—Shailendra Kumar
(74) *Attorney, Agent, or Firm*—Mark S. Cohen; Pearl Cohen Zedek Latzer, LLP

(57) ABSTRACT

This invention provides a class of androgen receptor targeting agents (ARTA). The compounds are selective androgen receptor modulators (SARM) useful for, inter-alia, suppressing spermatogenesis, treating a subject having a hormone related condition, treating a subject suffering from prostate cancer, delaying the progression of prostate cancer, preventing the recurrence of prostate cancer, and treating the recurrence of prostate cancer.

7 Claims, 1 Drawing Sheet

OTHER PUBLICATIONS

World Health Organization Task Force on Methods for the Regulation of Male Fertility, (1990) "Contracepive efficacy of testosterone-induced azoospermia in normal men". The Lancet, vol. 338, 955-959 and 1517-1518.

Francisco, et al (1990) "Long-acting contraceptive agents: testosterone esters of unsaturated acides", Steroids, vol. 55 Butterworths.

Hoberman, et al (1995) "The History of Synthetic Testosterone" Scientific American 76-81.

Kirkovsky, et al (1995) "Approaches to Irreversible non-steroidal chiral antiandrogens" Department of Pharmaceutical Sciences, University of Tennessee 47$^{th}$ Southeast/51$^{st}$ Southwest Joint Regional Meeting of the American Chemical Society, Memphis, TN.

Handelsman (1996) "Bridging the Gender Gap in Contraception: another hurldle cleared" The Medical Journal of Australia vol. 154, 230-233.

Edwards JP, et al (1999) Nonsteriodal androgen receptor agonists based on 4-(trifluromythyl1)-2H-pyrano [3, 2-g] quinolin-2-one Bioorg Med. Chem. Lett.9:1003.

Zhi L, et al (1999) Switching androgen receptor antiagonists to agonists by modifying C-ring substituents on piperidino [3,2-g]quinolone. Bioorg Med Chem. Lett. 1009.

Higuchi, et al (1999) 4-Alkyl—and 3,4-diakly1-1,2,3,4-tetrhydro-8-pyridono(5,6-g) quinolines: potent, nonsteriodal, androgen receptor agonists Bioorg. Med. Chem. Lett. 9:1335.

Hamann, et al (1999) Discovery of a potent, orally active nonsteriodal androgen receptor against: 4-ethyl-1, 2. 3, 4-tetrahydro-6-(trifluoromethyl)-8pyridono[5,6-g]-quinoline (LG121071). J Med Chem. 42: 210.

Rosen, et al (1995) Intracellular receptors and signal transducers and activators of transcription super families: novel targets for small-molecuile drug discovery. J Med. Chem. 38:4855.

Dalton, et al (1998) "Discovery of Nonsteroidal Androgens" Biochem Biophys Res Commun 244(1):1-4.

Edwards, et al (1998) New nonsteroidal androgen receptor modulators based on 4-(triflturomythyl)-2-(1H)-Pyrololidino[3,2-g]quinolone. Bioord Med Chem. Lett. 8:745.

Berger, et al (1975) "Concepts and Limitations in the application of radiolabled antiandrogens, estrogens, or androgens as isotropic scanning agents for the prostate" Invest. Urol 1391, 10-16.

Corey (1987) "Asymmetric Bromolactonization Reaction: Synthesis of Optically Active 2-Hydroxy-2-Methylalkanoic Acids from 2-Methylenealkanoic Acids" Tetrahedron Letters vol. 28, No. 25, 2801-2804.

* cited by examiner

SELECTIVE ANDROGEN RECEPTOR MODULATORS AND METHODS OF USE THEREOF

CROSS-REFERENCE TO RELATED APPLICATIONS

This application is a Continuation-In-Part application of U.S. application Ser. No. 10/462,837, filed Jun. 17, 2003, now U.S. Pat. No. 7,022,870, which claims the benefit of U.S. Provisional Application Ser. No. 60/388,739, filed Jun. 17, 2002, which are hereby incorporated by reference in their entirety.

FIELD OF INVENTION

The present invention relates to a novel class of androgen receptor targeting agents (ARTA) which demonstrate antiandrogenic activity, and comprise nonsteroidal ligands of the androgen receptor. The agents are useful in hormone therapy such as contraception, treating prostate cancer, treating hirsutism and others.

BACKGROUND OF THE INVENTION

The androgen receptor ("AR") is a ligand-activated transcriptional regulatory protein that mediates induction of male sexual development and function through its activity with endogenous androgens. Androgens are generally known as the male sex hormones. The androgenic hormones are steroids which are produced in the body by the testes and the cortex of the adrenal gland or can be synthesized in the laboratory. Androgenic steroids play an important role in many physiologic processes, including the development and maintenance of male sexual characteristics such as muscle and bone mass, prostate growth, spermatogenesis, and the male hair pattern (Matsumoto, Endocrinol. Met Clin. N. Am. 23:857-75 (1994)). The endogenous steroidal androgens include testosterone and dihydrotestosterone ("DHT"). Testosterone is the principal steroid secreted by the testes and is the primary circulating androgen found in the plasma of males. Testosterone is converted to DHT by the enzyme 5 alpha-reductase in many peripheral tissues. DHT is thus thought to serve as the intracellular mediator for most androgen actions (Zhou, et al., Molec. Endocrinol. 9:208-18 (1995)). Other steroidal androgens include esters of testosterone, such as the cypionate, propionate, phenylpropionate, cyclopentylpropionate, isocarporate, enanthate, and decanoate esters, and other synthetic androgens such as 7-Methyl-Nortestosterone ("MENT") and its acetate ester (Sundaram et al., "7 Alpha-Methyl-Nortestosterone(MENT): The Optimal Androgen For Male Contraception," Ann. Med., 25:199-205 (1993) ("Sundaram")). Because the AR is involved in male sexual development and function, the AR is a likely target for effecting male contraception or other forms of hormone replacement therapy.

Worldwide population growth and social awareness of family planning have stimulated a great deal of research in contraception. Contraception is a difficult subject under any circumstance. It is fraught with cultural and social stigma, religious implications, and, most certainly, significant health concerns. This situation is only exacerbated when the subject focuses on male contraception. Despite the availability of suitable contraceptive devices, historically, society has looked to women to be responsible for contraceptive decisions and their consequences. Although concern over sexually transmitted diseases has made men more aware of the need to develop safe and responsible sexual habits, women still often bear the brunt of contraceptive choice. Women have a number of choices, from temporary mechanical devices such as sponges and diaphragms to temporary chemical devices such as spermicides. Women also have at their disposal more permanent options, such as physical devices including IUDs and cervical caps as well as more permanent chemical treatments such as birth control pills and subcutaneous implants. However, to date, the only options available for men include the use of condoms and vasectomy. Condom use, however is not favored by many men because of the reduced sexual sensitivity, the interruption in sexual spontaneity, and the significant possibility of pregnancy caused by breakage or misuse. Vasectomies are also not favored. If more convenient methods of birth control were available to men, particularly long-term methods which require no preparative activity immediately prior to a sexual act, such methods could significantly increase the likelihood that men would take more responsibility for contraception.

Administration of the male sex steroids (e.g., testosterone and its derivatives) has shown particular promise in this regard due to the combined gonadotropin-suppressing and androgen-substituting properties of these compounds (Steinberger et al., "Effect of Chronic Administration of Testosterone Enanthate on Sperm Production and Plasma Testosterone, Follicle Stimulating Hormone, and Luteinizing Hormone Levels: A Preliminary Evaluation of a Possible Male Contraceptive, Fertility and Sterility 28:1320-28 (1977)). Chronic administration of high doses of testosterone completely abolishes sperm production (azoospermia) or reduces it to a very low level (oligospermia). The degree of spermatogenic suppression necessary to produce infertility is not precisely known. However, a recent report by the World Health Organization showed that weekly intramuscular injections of testosterone enanthate result in azoospermia or severe oligospermia (i.e., less than 3 million sperm per ml) and infertility in 98% of men receiving therapy (World Health Organization Task Force on Methods And Regulation of Male Fertility, "Contraceptive Efficacy of Testosterone-Induced Azoospermia and Oligospermia in Normal Men," Fertility and Sterility 65:821-29 (1996)).

Steroidal ligands which bind the AR and act as antiandrogens (e.g. cyproterone acetate) have been known for many years and are used clinically, with nonsteroidal antiandrogens in clinical use for hormone-dependent prostate cancer, less available.

SUMMARY OF THE INVENTION

In one embodiment, this invention provides a class of androgen receptor targeting agents (ARTA). The agents define a new subclass of compounds which are selective androgen receptor modulators (SARM) useful for oral testosterone replacement therapy. Several of the SARM compounds have been found to have an unexpected androgenic and anabolic activity of a nonsteroidal ligand for the androgen receptor. Other SARM compounds have been found to have an unexpected antiandrogenic activity of a nonsteroidal ligand for the androgen receptor.

In one embodiment, the present invention provides a selective androgen receptor modulator (SARM) compound represented by the structure of formula I:

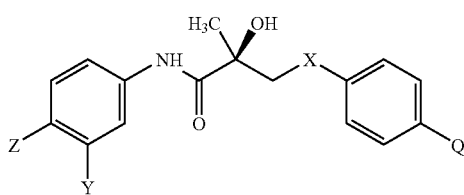

wherein
X is a O, CH₂, NH, Se, PR, or NR;
Z is NO₂, CN, COOH, COR, or CONHR;
Y is CF₃, F, I, Br, Cl, CN or SnR₃;
R is alkyl, haloalkyl, aryl, phenyl, halogen, alkenyl or OH; and
Q is alkyl, halogen, NR₂, NHCOCH₃, NHCOCF₃, NHCOR, NHCONHR, NHCOOR, OCONHR, CONHR, NHCSCH₃, NHCSCF₃, NHCSR NHSO₂CH₃, NHSO₂R, OR, COR, OCOR, OSO₂R, SO₂R or SR.

In another embodiment, the present invention provides an analog, derivative, isomer, metabolite, pharmaceutically acceptable salt, hydrate or N-oxide of the compound of formula I, or any combination thereof.

In one embodiment, X is NH. In another embodiment, Z is NO₂. In another embodiment, Z is CN. In another embodiment, Y is CF₃. In another embodiment, Q is NHCOCH₃. In another embodiment, Q is F.

In another embodiment, the present invention provides a selective androgen receptor modulator (SARM) compound represented by the structure of formula II:

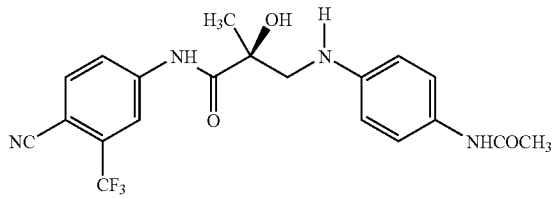

In another embodiment, the present invention provides an analog, derivative, isomer, metabolite, pharmaceutically acceptable salt, hydrate or N-oxide of the compound of formula II, or any combination thereof.

In another embodiment, the present invention provides a selective androgen receptor modulator (SARM) compound represented by the structure of formula III:

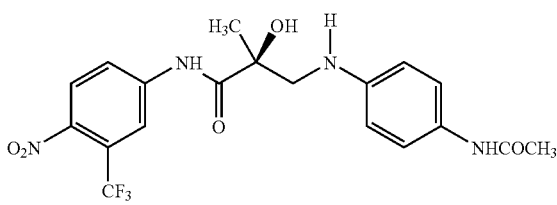

In another embodiment, the present invention provides an analog, derivative, isomer, metabolite, pharmaceutically acceptable salt, hydrate or N-oxide of the compound of formula III, or any combination thereof.

In another embodiment, the present invention provides a selective androgen receptor modulator (SARM) compound represented by the structure of formula IV:

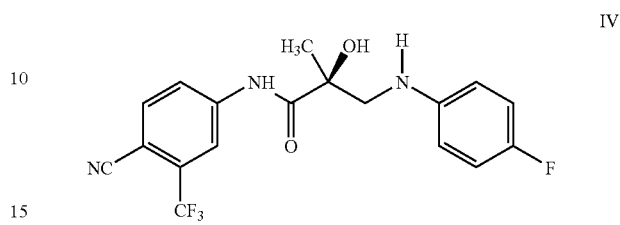

In another embodiment, the present invention provides an analog, derivative, isomer, metabolite, pharmaceutically acceptable salt, hydrate or N-oxide of the compound of formula IV, or any combination thereof.

In another embodiment, the present invention provides a selective androgen receptor modulator (SARM) compound represented by the structure of formula V:

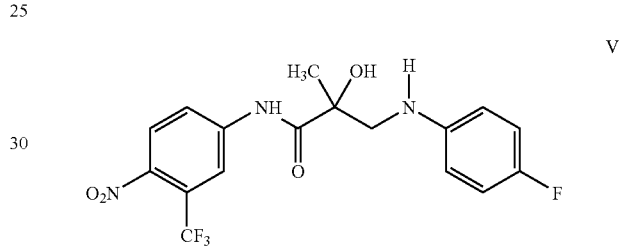

In another embodiment, the present invention provides an analog, derivative, isomer, metabolite, pharmaceutically acceptable salt, hydrate or N-oxide of the compound of formula V, or any combination thereof.

In one embodiment, the SARM compound of any of formulas I-V is an androgen receptor agonist. In another embodiment, the SARM compound of any of formulas I-V is an androgen receptor antagonist.

In one embodiment, the present invention further provides a method of binding a selective androgen receptor modulator compound to an androgen receptor, comprising the step of contacting the androgen receptor with the selective androgen receptor modulator compound of any of formulas I-V, and/or its analog, derivative, isomer, metabolite, pharmaceutically acceptable salt, hydrate of N-oxide or any combination thereof, in an amount effective to bind the selective androgen receptor modulator compound to the androgen receptor.

In one embodiment, the present invention provides a method of suppressing spermatogenesis in a subject, comprising the step of contacting an androgen receptor of the subject with the selective androgen receptor modulator compound of any of formulas I-V and/or its analog, derivative, isomer, metabolite, pharmaceutically acceptable salt, hydrate or N-oxide or any combination thereof, in an amount effective to suppress sperm production.

In one embodiment, the present invention further provides a method of hormone therapy, comprising the step of contacting an androgen receptor of a subject with the selective androgen receptor modulator compound of any of formulas I-V and/or its analog, derivative, isomer, metabolite, pharmaceutically acceptable salt, hydrate or N-oxide or any combination thereof, in an amount effective to bind the selective androgen receptor modulator compound to the androgen receptor and effect a change in an androgen-dependent condition.

In one embodiment, the present invention further provides a method of treating a subject having a hormone related condition, comprising the step of administering to the subject the selective androgen receptor modulator compound of any of formulas I-V and/or its analog, derivative, isomer, metabolite, pharmaceutically acceptable salt, hydrate or N-oxide or any combination thereof, in an amount effective to bind the selective androgen receptor modulator compound to the androgen receptor and effect a change in an androgen-dependent condition.

In one embodiment, the present invention further provides a method of treating a subject suffering from prostate cancer, comprising the step of administering to the subject the selective androgen receptor modulator compound of any of formulas I-V, and/or its analog, derivative, isomer, metabolite, pharmaceutically acceptable salt, hydrate or N-oxide or any combination thereof, in an amount effective to treat prostate cancer in the subject.

In one embodiment, the present invention further provides a method of delaying the progression of prostate cancer in a subject suffering from prostate cancer, comprising the step of administering to the subject the selective androgen receptor modulator compound of any of formulas I-V, and/or its analog, derivative, isomer, metabolite, pharmaceutically acceptable salt, hydrate or N-oxide or any combination thereof, in an amount effective to delay the progression of prostate cancer in the subject.

In one embodiment, the present invention further provides a method of preventing the recurrence of prostate cancer in a subject suffering from prostate cancer, comprising the step of administering to the subject the selective androgen receptor modulator compound of any of formulas I-V, and/or its analog, derivative, isomer, metabolite, pharmaceutically acceptable salt, hydrate or N-oxide or any combination thereof, in an amount effective to prevent the recurrence of prostate cancer in the subject.

In one embodiment, the present invention provides a method of treating the recurrence of prostate cancer in a subject suffering from prostate cancer, comprising the step of administering to the subject the selective androgen receptor modulator compound of any of formulas I-V, and/or its analog, derivative, isomer, metabolite, pharmaceutically acceptable salt, hydrate or N-oxide or any combination thereof, in an amount effective to treat the recurrence of prostate cancer in the subject.

The novel selective androgen receptor modulator compounds of the present invention, either alone or as a composition, are useful as a male contraceptive or in the treatment of a variety of hormone-related conditions, such as hypogonadism, sarcopenia, erythropoiesis, and osteoporosis. Further, the selective androgen receptor modulator compounds are useful for oral testosterone replacement therapy.

The selective androgen receptor modulator compounds of the present invention offer a significant advance over steroidal androgen treatment. Several of the selective androgen receptor modulator compounds of the present invention have unexpected androgenic and anabolic activity of a nonsteroidal ligand for the androgen receptor. Other selective androgen receptor modulator compounds of the present invention have unexpected antiandrogenic activity of a nonsteroidal ligand for the androgen receptor. Thus, treatment with the selective androgen receptor modulator compounds of the present invention will not be accompanied by serious side effects, inconvenient modes of administration, or high costs and will still have the advantages of oral bioavailability, lack of cross-reactivity with other steroid receptors, and long biological half-lives.

BRIEF DESCRIPTION OF THE DRAWINGS

The present invention will be understood and appreciated more fully from the following detailed description taken in conjunction with the appended drawing.

DETAILED DESCRIPTION OF THE INVENTION

Figure 1:
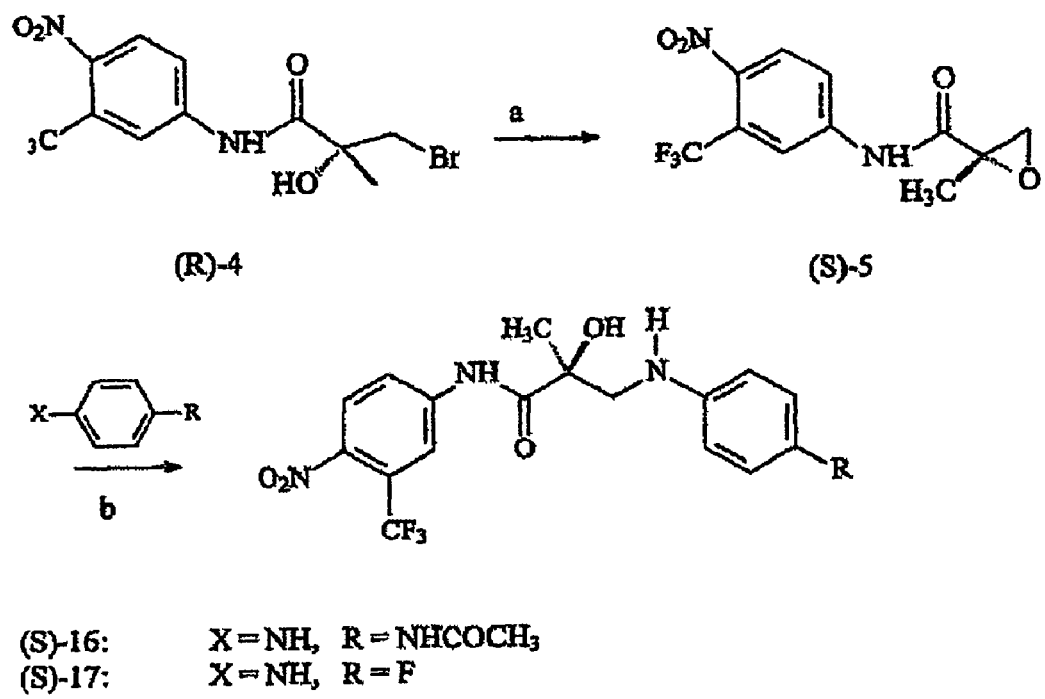
FIG. 1: Synthetic scheme of nitrogen-linked selective androgen modulator compounds. a) Acetone/$K_2CO_3$ reflux b) hexafluoro-isopropanol, reflux.

In one embodiment, this invention provides a class of androgen receptor targeting agents (ARTA). The agents define a new subclass of compounds which are selective androgen receptor modulators (SARM) useful for oral testosterone replacement therapy. Several of the SARM compounds have been found to have an unexpected androgenic and anabolic activity of a nonsteroidal ligand for the androgen receptor. Other SARM compounds have been found to have an unexpected antiandrogenic activity of a nonsteroidal ligand for the androgen receptor. In one embodiment, the SARM compounds bind irreversibly to the androgen receptor. In another embodiment, the SARM compounds bind reversibly to the androgen receptor. The novel selective androgen receptor modulator compounds of the present invention, either alone or as a composition, are useful for suppressing spermatogenesis, treating a subject having a hormone related condition, treating a subject suffering from prostate cancer, delaying the progression of prostate cancer, preventing the recurrence of prostate cancer, and treating the recurrence of prostate cancer.

In one embodiment, the present invention provides a selective androgen receptor modulator (SARM) compound represented by the structure of formula I:

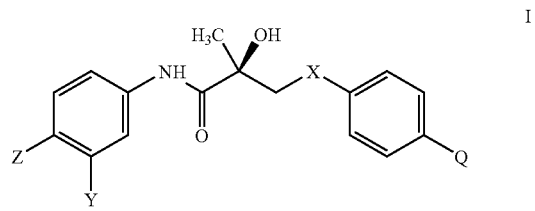

wherein

X is a O, $CH_2$, NH, Se, PR, or NR;

Z is $NO_2$, CN, COOH, COR, or CONHR;

Y is $CF_3$, F, I, Br, Cl, CN or $SnR_3$;

R is alkyl, haloalkyl, aryl, phenyl, halogen, alkenyl or OH; and

Q is alkyl, halogen, $NR_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$ or SR.

In one embodiment, this invention provides an analog of the compound of formula I. In another embodiment, this invention provides a derivative of the compound of formula I.

In another embodiment, this invention provides an isomer of the compound of formula I. In another embodiment, this invention provides a metabolite of the compound of formula I. In another embodiment, this invention provides a pharmaceutically acceptable salt of the compound of formula I. In another embodiment, this invention provides a hydrate of the compound of formula I. In another embodiment, this invention provides an N-oxide of the compound of formula I. In another embodiment, this invention provides a combination of any of an analog, derivative, metabolite, isomer, pharmaceutically acceptable salt, hydrate or N-oxide of the compound of formula I.

In one embodiment, the present invention provides a SARM compound of formula I wherein X is NH. In another embodiment, the SARM compound is a compound of formula I wherein Z is $NO_2$. In another embodiment, the SARM compound is a compound of formula I wherein Z is CN. In another embodiment, the SARM compound is a compound of formula I wherein Y is $CF_3$. In another embodiment, the SARM compound is a compound of formula I wherein Q is $NHCOCH_3$. In another embodiment, the SARM compound is a compound of formula I wherein $R_2$ is CN. In another embodiment, the SARM compound is a compound of formula I, II or III wherein Q is F.

In another embodiment, the present invention provides a selective androgen receptor modulator (SARM) compound represented by the structure of formula II:

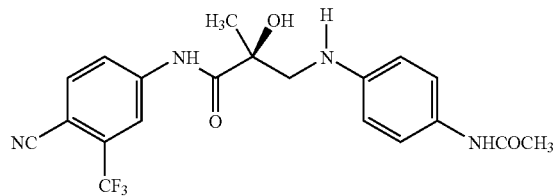

In one embodiment, this invention provides an analog of the compound of formula II. In another embodiment, this invention provides a derivative of the compound of formula II. In another embodiment, this invention provides an isomer of the compound of formula II. In another embodiment, this invention provides a metabolite of the compound of formula II. In another embodiment, this invention provides a pharmaceutically acceptable salt of the compound of formula II. In another embodiment, this invention provides a hydrate of the compound of formula II. In another embodiment, this invention provides an N-oxide of the compound of formula II.

In another embodiment, this invention provides a combination of any of an analog, derivative, metabolite, isomer, pharmaceutically acceptable salt, hydrate or N-oxide of the compound of formula II.

In one embodiment, the compound of formula II is an antiandrogen. In one embodiment, the compound of formula II has minimal androgen receptor agonist activity.

In another embodiment, the present invention provides a selective androgen receptor modulator (SARM) compound represented by the structure of formula III:

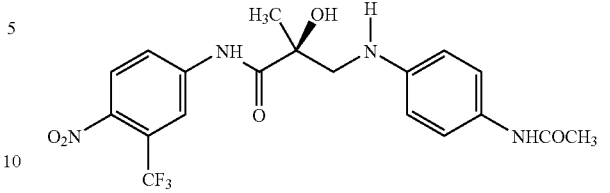

In one embodiment, this invention provides an analog of the compound of formula III. In another embodiment, this invention provides a derivative of the compound of formula III. In another embodiment, this invention provides an isomer of the compound of formula III. In another embodiment this invention provides a metabolite of the compound of formula III. In another embodiment, this invention provides a pharmaceutically acceptable salt of the compound of formula III. In another embodiment, this invention provides a hydrate of the compound of formula III. In another embodiment, this invention provides an N-oxide of the compound of formula III. In another embodiment, this invention provides a combination of any of an analog, derivative, metabolite, isomer, pharmaceutically acceptable salt, hydrate or N-oxide of the compound of formula III.

In one embodiment, the compound of formula III is an antiandrogen. In one embodiment, the compound of formula III has minimal androgen receptor agonist activity.

In another embodiment, the present invention provides a selective androgen receptor modulator (SARM) compound represented by the structure of formula IV:

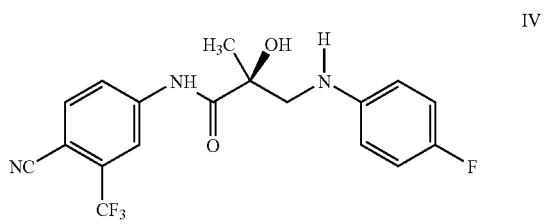

In one embodiment, this invention provides an analog of the compound of formula IV. In another embodiment, this invention provides a derivative of the compound of formula IV. In another embodiment, this invention provides an isomer of the compound of formula IV. In another embodiment, this invention provides a metabolite of the compound of formula IV. In another embodiment, this invention provides a pharmaceutically acceptable salt of the compound of formula IV. In another embodiment, this invention provides a hydrate of the compound of formula IV. In another embodiment, this invention provides an N-oxide of the compound of formula IV. In another embodiment, this invention provides a combination of any of an analog, derivative, metabolite, isomer, pharmaceutically acceptable salt, hydrate or N-oxide of the compound of formula IV.

In one embodiment, the compound of formula IV is an antiandrogen. In one embodiment, the compound of formula IV has minimal androgen receptor agonist activity.

In another embodiment, the present invention provides a selective androgen receptor modulator (SARM) compound represented by the structure of formula V:

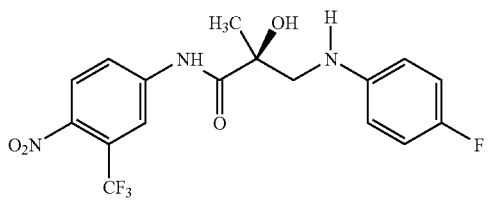

V

In one embodiment, this invention provides an analog of the compound of formula V. In another embodiment, this invention provides a derivative of the compound of formula V. In another embodiment, this invention provides an isomer of the compound of formula V. In another embodiment, this invention provides a metabolite of the compound of formula V. In another embodiment, this invention provides a pharmaceutically acceptable salt of the compound of formula V. In another embodiment, this invention provides a hydrate of the compound of formula V. In another embodiment, this invention provides an N-oxide of the compound of formula V. In another embodiment, this invention provides a combination of any of an analog, derivative, metabolite, isomer, pharmaceutically acceptable salt, hydrate or N-oxide of the compound of formula V.

In one embodiment, the compound of formula V is an antiandrogen. In one embodiment, the compound of formula V has minimal androgen receptor agonist activity.

The substituent R is defined herein as an alkyl, a haloalkyl, aryl, phenyl, halo, alkenyl or hydroxyl.

An "alkyl" group refers to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

An "alkenyl" group refers to an unsaturated hydrocarbon, including straight chain, branched chain and cyclic groups having one or more double bond. The alkenyl group may have one double bond, two double bonds, three double bonds etc. Examples of alkenyl groups are ethenyl, propenyl, butenyl, cyclohexenyl etc. The alkenyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

A "haloalkyl" group refers to an alkyl group as defined above, which is substituted by one or more halogen atoms, e.g. by F, Cl, Br or I.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

A "hydroxyl" group refers to an OH group. An "alkenyl" group refers to a group having at least one carbon to carbon double bond. A halo group refers to F, Cl, Br or I.

An "arylalkyl" group refers to an alkyl bound to an aryl, wherein alkyl and aryl are as defined above. An example of an arylalkyl group is a benzyl group.

As contemplated herein, the present invention relates to the use of a SARM compound and/or its analog, derivative, isomer, metabolite, pharmaceutically acceptable salt, hydrate, N-oxide, or combinations thereof. In one embodiment, the invention relates to the use of an analog of the SARM compound. In another embodiment, the invention relates to the use of a derivative of the SARM compound. In another embodiment, the invention relates to the use of an isomer of the SARM compound. In another embodiment, the invention relates to the use of a metabolite of the SARM compound. In another embodiment, the invention relates to the use of a pharmaceutically acceptable salt of the SARM compound. In another embodiment, the invention relates to the use of a hydrate of the SARM compound. In another embodiment, the invention relates to the use of an N-oxide of the SARM compound.

As defined herein, the term "isomer" includes, but is not limited to, optical isomers and analogs, structural isomers and analogs, conformational isomers and analogs, and the like.

In one embodiment, this invention encompasses the use of various optical isomers of the SARM compound. It will be appreciated by those skilled in the art that the SARMs of the present invention contain at least one chiral center. Accordingly, the SARMs used in the methods of the present invention may exist in, and be isolated in, optically-active or racemic forms. Some compounds may also exhibit polymorphism. It is to be understood that the present invention encompasses any racemic, optically-active, polymorphic, or stereoisomeric form, or mixtures thereof, which form possesses properties useful in the treatment of androgen-related conditions described herein. In one embodiment, the SARMs are the pure (R)-isomers. In another embodiment, the SARMs are the pure (S)-isomers. In another embodiment, the SARMs are a mixture of the (R) and the (S) isomers. In another embodiment, the SARMs are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

In one embodiment, this invention encompasses the use of various structural isomers of the SARM compound. It will be appreciated by those skilled in the art that the SARMs of the present invention may exist as the (Z)- or the (E)-isomers. The invention encompasses pure (Z)- and (E)-isomers of the SARM compounds defined herein and mixtures thereof.

The invention includes pharmaceutically acceptable salts of amino-substituted compounds with organic and inorganic acids, for example, citric acid and hydrochloric acid. The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters.

This invention further includes derivatives of the SARM compounds. The term "derivatives" includes but is not limited to ether derivatives, acid derivatives, amide derivatives, ester derivatives and the like. In addition, this invention further includes hydrates of the SARM compounds. The term "hydrate" includes but is not limited to hemihydrate, monohydrate, dihydrate, trihydrate and the like.

This invention further includes metabolites of the SARM compounds. The term "metabolite" means any substance produced from another substance by metabolism or a metabolic process.

As used herein, receptors for extracellular signaling molecules are collectively referred to as "cell signaling receptors". Many cell signaling receptors are transmembrane proteins on a cell surface; when they bind an extracellular signaling molecule (i.e., a ligand), they become activated so as to generate a cascade of intracellular signals that alter the behavior of the cell. In contrast, in some cases, the receptors are inside the cell and the signaling ligand has to enter the cell to activate them; these signaling molecules therefore must be sufficiently small and hydrophobic to diffuse across the plasma membrane of the cell.

Steroid hormones are one example of small hydrophobic molecules that diffuse directly across the plasma membrane of target cells and bind to intracellular cell signaling receptors. These receptors are structurally related and constitute the intracellular receptor superfamily (or steroid-hormone receptor superfamily). Steroid hormone receptors include progesterone receptors, estrogen receptors, androgen receptors, glucocorticoid receptors, and mineralocorticoid receptors. The present invention is particularly directed to androgen receptors.

In addition to ligand binding to the receptors, the receptors can be blocked to prevent ligand binding. When a substance binds to a receptor, the three-dimensional structure of the substance fits into a space created by the three-dimensional structure of the receptor in a ball and socket configuration. The better the ball fits into the socket, the more tightly it is held. This phenomenon is called affinity. If the affinity of a substance is greater than the original hormone, it will compete with the hormone and bind the binding site more frequently. Once bound, signals may be sent through the receptor into the cell, causing the cell to respond in some fashion. This is called activation. On activation, the activated receptor then directly regulates the transcription of specific genes. But the substance and the receptor may have certain attributes, other than affinity, in order to activate the cell. Chemical bonds between atoms of the substance and the atoms of the receptors may form. In some cases, this leads to a change in the configuration of the receptor, which is enough to begin the activation process (called signal transduction).

In one embodiment, the present invention is directed to selective androgen receptor modulator compounds which are agonist compounds. A receptor agonist is a substance which binds receptors and activates them. Thus, in one embodiment, the SARM compounds of the present invention are useful in binding to and activating steroidal hormone receptors. In one embodiment, the agonist compound of the present invention is an agonist which binds the androgen receptor. In another embodiment, the compound has high affinity for the androgen receptor. In another embodiment, the agonist compound also has anabolic activity. In another embodiment, the present invention provides selective androgen modulator compounds which have agonistic and anabolic activity of a nonsteroidal compound for the androgen receptor.

In another embodiment, the present invention is directed to selective androgen receptor modulator compounds which are antagonist compounds. A receptor antagonist is a substance which binds receptors and inactivates them. Thus, in one embodiment, the SARM compounds of the present invention are useful in binding to and inactivating steroidal hormone receptors. In one embodiment, the antagonist compound of the present invention is an antagonist which binds the androgen receptor. In another embodiment, the compound has a high affinity for the androgen receptor. In some embodiments, SARM compounds possessing antagonist activity are also referred to herein as "antiandrogens". In some embodiments, antiandrogenic compounds of this invention possess greater antagonists rather than agonist activity of the androgen receptor, however, the compounds nonetheless possess agonist activity.

In some embodiments, antagonist versus agonist activity is determined as a function of the activity of the compounds in androgen receptor transcriptional activation assays. In one embodiment, compounds inducing about 30%, or less, transcriptional activation in such assays, for example, as described hereinbelow, are characterized as antagonists or antiandrogens.

In another embodiment, the SARM compounds of the present invention can be classified as partial AR agonist/antagonists. The SARMs are AR agonists in some tissues, to cause increased transcription of AR-responsive genes (e.g. muscle anabolic effect). In other tissues, these compounds serve as inhibitors at the AR to prevent agonistic effects of the native androgens.

Assays to determine whether the compounds of the present invention are AR agonists or antagonists are well known to a person skilled in the art. For example, AR agonistic activity can be determined by monitoring the ability of the SARM compounds to maintain and/or stimulate the growth of AR containing tissue such as prostate and seminal vesicles, as measured by weight. AR antagonistic activity can be determined by monitoring the ability of the SARM compounds to inhibit the growth of AR containing tissue.

The compounds of the present invention bind either reversibly or irreversibly to an androgen receptor. In one embodiment, the androgen receptor is an androgen receptor of a mammal. In another embodiment, the androgen receptor is an androgen receptor of a human. In one embodiment, the SARM compounds bind reversibly to the androgen receptor of a mammal, for example a human. Reversible binding of a compound to a receptor means that a compound can detach from the receptor after binding.

In another embodiment, the SARM compounds bind irreversibly to the androgen receptor of a mammal, for example a human. Thus, in one embodiment, the compounds of the present invention may contain a functional group (e.g. affinity label) that allows alkylation of the androgen receptor (i.e. covalent bond formation). Thus, in this case, the compounds are alkylating agents which bind irreversibly to the receptor and, accordingly, cannot be displaced by a steroid, such as the endogenous ligands DHT and testosterone. An "alkylating agent" is defined herein as an agent which alkylates (forms a covalent bond) with a cellular component, such as DNA, RNA or enzyme. It is a highly reactive chemical that introduces alkyl radicals into biologically active molecules and thereby prevents their proper functioning. The alkylating moiety is an electrophilic group that interacts with nucleophilic moieties in cellular components.

According to one embodiment of the present invention, a method is provided for binding the SARM compounds of the present invention to an androgen receptor by contacting the receptor with a SARM compound and/or its analog, derivative, isomer, metabolite, pharmaceutically acceptable salt, hydrate or N-oxide or any combination thereof, under conditions effective to cause the selective androgen receptor modulator compound to bind the androgen receptor. The binding of the selective androgen receptor modulator compounds to the androgen receptor enables the compounds of the present invention to be useful as a male contraceptive and in a number of hormone therapies. The agonist compounds bind to and activate the androgen receptor. The antagonist compounds bind to and inactivate the androgen receptor. Binding of the agonist or antagonist compounds is either reversible or irreversible.

According to one embodiment of the present invention, a method is provided for suppressing spermatogenesis in a subject by contacting an androgen receptor of the subject with a SARM compound of the present invention and/or its analog, derivative, isomer, metabolite, pharmaceutically acceptable salt, hydrate or N-oxide or any combination thereof, in an amount effective to bind the selective androgen receptor modulator compound to the androgen receptor and suppress spermatogenesis.

According to another embodiment of the present invention, a method is provided for hormonal therapy in a patient (i.e., one suffering from an androgen-dependent condition) which includes contacting an androgen receptor of a patient with a SARM compound of the present invention and/or its analog, derivative, isomer, metabolite, pharmaceutically acceptable salt, hydrate or N-oxide or any combination thereof, in an amount effective to bind the selective androgen receptor modulator compound to the androgen receptor and effect a change in an androgen-dependent condition.

According to another embodiment of the present invention, a method is provided for treating a subject having a hormone related condition which includes administering to the subject a SARM compound of the present invention and/or its analog, derivative, isomer, metabolite, pharmaceutically acceptable salt, hydrate or N-oxide or any combination thereof, in an amount effective to bind the SARM compound to the androgen receptor and effect a change in an androgen-dependent condition.

Androgen-dependent conditions which may be treated according to the present invention include those conditions which are associated with aging, such as hypogonadism, sarcopenia, erythropoiesis, osteoporosis, and any other conditions determined to be dependent upon low androgen (e.g., testosterone) levels.

According to another embodiment of the present invention, a method is provided for treating a subject suffering from prostate cancer, comprising the step of administering to the subject a SARM compound of the present invention and/or its analog, derivative, isomer, metabolite, pharmaceutically acceptable salt, hydrate or N-oxide or any combination thereof, in an amount effective to treat prostate cancer in the subject.

According to another embodiment of the present invention, a method is provided for delaying the progression of prostate cancer in a subject suffering from prostate cancer, comprising the step of administering to the subject a SARM compound of the present invention and/or its analog, derivative, isomer, metabolite, pharmaceutically acceptable salt, hydrate or N-oxide or any combination thereof, in an amount effective to delay the progression of prostate cancer in the subject.

According to another embodiment of the present invention, a method is provided for preventing the recurrence of prostate cancer in a subject suffering from prostate cancer, comprising the step of administering to the subject a SARM compound of the present invention and/or its analog, derivative, isomer, metabolite, pharmaceutically acceptable salt, hydrate or N-oxide or any combination thereof, in an amount effective to prevent the recurrence of prostate cancer in the subject.

According to another embodiment of the present invention, a method is provided for treating the recurrence of prostate cancer in a subject suffering from prostate cancer, comprising the step of administering to the subject a SARM compound of the present invention and/or its analog, derivative, isomer, metabolite, pharmaceutically acceptable salt, hydrate or N-oxide or any combination thereof, in an amount effective to treat the recurrence of prostate cancer in the subject.

As defined herein, "contacting" means that the SARM compound of the present invention is introduced into a sample containing the enzyme in a test tube, flask, tissue culture, chip, array, plate, microplate, capillary, or the like, and incubated at a temperature and time sufficient to permit binding of the SARM to the enzyme. Methods for contacting the samples with the SARM or other specific binding components are known to those skilled in the art and may be selected depending on the type of assay protocol to be run. Incubation methods are also standard and are known to those skilled in the art.

In another embodiment, the term "contacting" means that the SARM compound of the present invention is introduced into a subject receiving treatment, and the SARM compound is allowed to come in contact with the androgen receptor in vivo.

As used herein, the term "treating" includes preventative as well as disorder remitative treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

As used herein, the term "administering" refers to bringing a subject in contact with a SARM compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a subject.

In one embodiment, the methods of the present invention comprise administering a SARM compound as the sole active ingredient. However, also encompassed within the scope of the present invention are methods for hormone therapy, for treating prostate cancer, for delaying the progression of prostate cancer, and for preventing and/or treating the recurrence of prostate cancer, which comprise administering the SARM compounds in combination with one or more therapeutic agents. These agents include, but are not limited to: LHRH analogs, reversible antiandrogens, antiestrogens, anticancer drugs, 5-alpha reductase inhibitors, aromatase inhibitors, progestins, or agents acting through other nuclear hormone receptors.

Thus, in one embodiment, the present invention provides compositions and pharmaceutical compositions comprising a selective androgen receptor modulator compound, in combination with an LHRH analog. In another embodiment, the present invention provides compositions and pharmaceutical compositions comprising a selective androgen receptor modulator compound, in combination with a reversible antiandrogen. In another embodiment, the present invention provides compositions and pharmaceutical compositions comprising a selective androgen receptor modulator compound, in combination with an antiestrogen. In another embodiment, the present invention provides compositions and pharmaceutical compositions comprising a selective androgen receptor modulator compound, in combination with an anticancer drug. In another embodiment, the present invention provides compositions and pharmaceutical compositions comprising a selective androgen receptor modulator compound, in combination with a 5-alpha reductase inhibitor. In another embodiment, the present invention provides compositions and pharmaceutical compositions comprising a selective androgen receptor modulator compound, in combination with an aromatase inhibitor. In another embodiment, the present invention provides compositions and pharmaceutical compositions comprising a selective androgen receptor modulator compound, in combination with a progestin. In another embodiment, the present invention provides compositions and pharmaceutical compositions comprising a selective androgen receptor modulator compound, in combination with an agent acting through other nuclear hormone receptors.

As used herein, "pharmaceutical composition" means therapeutically effective amounts of the SARM together with suitable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or Lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance. Controlled or sustained release compositions include formulation in lipophilic depots (e.g., fatty acids, waxes, oils).

Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal and oral. In one embodiment the pharmaceutical composition is administered parenterally, paracancerally, transmucosally, transdermally, intramuscularly, intravenously, intradermally, subcutaneously, intraperitonealy, intraventricularly, intracranially or intratumorally.

Further, as used herein "pharmaceutically acceptable carriers" are well known to those skilled in the art and include, but are not limited to, 0.01-0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions of the invention incorporate particulate forms, protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

The pharmaceutical preparation can comprise the SARM agent alone, or can further include a pharmaceutically acceptable carrier and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the SARM agent can be administered to a subject by, for example, subcutaneous implantation of a pellet; in one embodiment, the pellet provides for controlled release of SARM agent over a period of time. The preparation can also be administered by intravenous, intraarterial, or intramuscular injection of a liquid preparation, oral administration of a liquid or solid preparation, or by topical application. Administration can also be accomplished by use of a rectal suppository or a urethral suppository.

The pharmaceutical preparations of the invention can be prepared by known dissolving, mixing, granulating, or tablet-forming processes. For oral administration, the SARM agents or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the SARM agents or their physiologically tolerated derivatives such as salts, esters, N-oxides, and the like are converted into a solution, suspension, or emulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Typically, such compositions are prepared as aerosols of the polypeptide delivered to the nasopharynx or as injectables, either as liquid solutions or suspensions; however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, the SARM agents or their physiologically tolerated derivatives such as salts, esters, N-oxides, and the like can be prepared and applied as solutions, suspensions, or emulsions in a physiologically acceptable diluent with or without a pharmaceutical carrier.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

For use in medicine, the salts of the SARM may be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic: acid, oxalic acid, citric acid, tartaric acid, carbonic acid or phosphoric acid.

The following examples are presented in order to more fully illustrate the preferred embodiments of the invention. They should in no way be construed, however, as limiting the broad scope of the invention.

EXPERIMENTAL DETAILS SECTION

Example 1

Synthesis of N-Bridged Selective Androgen Modulator Compounds

A. Chemistry

N-bridged selective androgen modulator compounds (SARMs) of the present invention were synthesized according to Scheme 1 (FIG. 1). Initially, the syntheses were performed in two separate steps—isolating epoxide (S)-5 before epoxide opening. These steps were combined to a two-step one-pot process where, after the expoxide was formed, the solvent was removed and the resulting residue was immediately carried on to the opening step. By TLC, the first step goes cleanly and completely to the epoxide. The epoxide was opened with the appropriate substituted aniline in hexafluoro-isopropanol. Aromatic amines are extremely non-nucleophilic; thus the epoxide had to be formed and opened in the presence of hexafluoro-isopropanol, which increases the electrophilicity of the epoxide.

B. Synthesis

S-3-(4-Acetylamino-phenylamino)-2-hydroxy-2-methyl-N-(4-nitro-3-trifluoromethylphenyl)propionamide (S)-16. (S)-5 (0.075 g, 0.26 mmol) and (4-aminophenyl)acetamide (0.04 g, 0.26 mmol) were dissolved in 1.5 ml of hexafluoro-2-propanol, and the mixture was allowed to stir at room temperature until the reaction was complete. Completeness of the reaction was monitored by the disappearance of the epoxide starting material, as determined by TLC. The solvent was evaporated, and the residue was diluted with 30 ml of water. This aqueous phase was extracted with three 30 ml portions of EtOAc. The combined EtOAc extracts were dried over MgSO4, and evaporated to give an oil. By TLC, the oil showed several intense spots. Preparative TLC was used to purify (S)-16 with 10% methanol in chloroform as the mobile phase. The title compound (25 mg, 0.06 mmol) was obtained as a tan powder. (27%); mp 143-145° C.; $^1$H NMR (DMSO-$d_6$) ? 10.48 (s, 1H, NH), 9.48 (s, 1H, NH), 8.48 (s, 1H, ArH), 9.28 (d, J=9 Hz, J-2 Hz, 1H, ArH), 8.16 (d, J=9 Hz, 1H, ArH), 7.21 (d, J=8 Hz, 2H, ArH), 6.57 (d, J=8.0 Hz, 2H, ArH), 6.06 (s, 1H, OH), 5.1 (bs, 1H, NH), 3.41 (dd, J-12, 3 Hz, 1H, (CH$_2$(1)), 3.11 (dd, J=12, 3 Hz, 1H, (CH$_2$(2)), 1.93 (s, 3H, Me), 1.41 (s, 3H, Me); Analysis ($C_{19}H_{19}F_3N_4O_5$) Calculated: C, 52.74%; H, 4.89%; N, 11.58%. Found: C, 52.4%; H, 4.9%; N, 11.2%. Calculated Mass 440.13, [M-H]438.8.

S-3-(4-Fluoro-phenylamino)-2-hydroxy-2-methyl-N-(4-nitro-3-trifluoromethylphenyl)propionamide (S)-16. (S)-5 (0.05 g, 0.1 mmol) and (4-fluoroaniline (16 ?l, 0.17 mmol) were dissolved in 1 ml of hexafluoro-2-propanol, and the mixture was mixed at reflux overnight. The workup was the same as for (S)-15, giving an oil that hardened to a glass on standing. The oil was purified on silica gel column with EtOAc/hexanes (1:1) as the mobile phase to give the title compound as an amber-colored oil (25 mg, 0.06 mmol) (36%); $^1$H NMR (CDCl$_3$) ? 9.22 (s, 1H, NH), 8.05 (m, 3H, ArH), 6.9 (m, 2H, ArH), 6.7 (m, 2H, ArH), 3.84 (d, J=13 Hz, 1H, (CH$_2$(1)), 3.8 (s, 1H, OH), 3.6 (bs, 1H, NH), 3.24 (d, J=13 Hz, 1H, (CH$_2$(2)), 1.58 (s, 3H, Me); Analysis (C$_{17}$H$_{15}$F$_4$N$_3$O$_4$.0.25 Acetone) Calculated: C, 51.27%; H, 4.0%; N, 10.10%. Found: C, 51.05%; H, 3.96%; N, 9.90%. Calculated Mass 401, [M-H]400.2.

Example 2

Androgen Receptor Binding Affinities Of N-Bridged Selective Androgen Modulator Compounds Methods AR binding affinities were determined using competitive binding assays as described previously (Kirkovsky, L. et al, Chiral nonsteroidal affinity ligands for the androgen receptor. Bicalutamide analogues bearing electrophilic groups in the B aromatic ring. *J. Med. Chem.* 2000, 43, 581-590). Briefly, AR binding studies were performed by incubating increasing concentrations (10$^{-3}$) nM to 10,000 nM) of each ligand with cytosol, and a saturating concentration of $^3$H-mibolerone (MIB) (1 nm) at 4° C. for 18 h. The incubates also contained 1,000 nM triamcinolone acetonide to block interaction of MIB with progesterone receptors. For the determination of non-specific binding, separate experiments were conducted by adding 1,000 nM MIB to the incubate. Separation of bound and free radioactivity at the end of incubation was achieved by the hydroxyapatite method. A 0.8 mL portion of the ethanolic supernatant was added to 5 mL of scintillation cocktail. Radioactivity was counted in a Beckman LS 6800 liquid scintillation counter.

The Androgen Receptor (AR) binding affinities of the N-bridged compounds (S)-16 and (S-17) were determined.

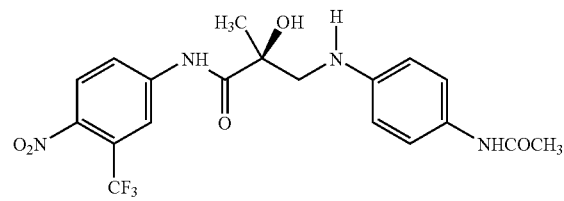

(S)-16

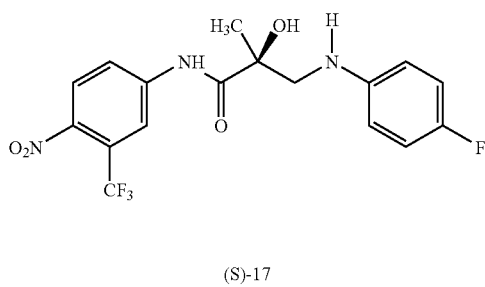

(S)-17

The AR binding affinities are summarized in Table 1. Compound (S)-16 displayed a moderate affinity for the AR, while (S)-17 displayed a high affinity for the AR.

TABLE 1

| Compound | Ki (nm) |
|---|---|
| (S)-16 | 135 ± 12 |
| (S)-17 | 10 ± 1 |

Example 2

Compounds 1 and 2 were synthesized as described herein, and tested for affinity and in vitro functional activity. Intact AR binding affinities were determined using a competitive binding assay using rat ventral prostate cytosol as the source for AR, as described previously (Schroder, F. H. Pure Antiandrogens as Monotherapy in Prospective Studies of Prostatic Carcinoma; Prog. Clin. Biol. Res. 1990, 359, 93-107). Intact AR in vitro functional activity was examined using a cotransfection assay as previously described, utilizing 10 nM of the SARM and activity was expressed as a % maximum transcriptional activation observed for 1 nM dihydrotestosterone (Dalton, J. T.; Mukherjee, A.; Zhu, Z.; Kirkovsky, L.; Miller, D. D. Discovery of Nonsteroidal Androgens. Biochem. Biophys. Res. Comm. 1998, 244, 1-4).

Compounds that induced at least 70% maximum transcriptional activation were considered as full agonists whereas partial agonists had to induce at least 30%, and antagonist induced less than 30% of the transcriptional activation of 1 nM DHT.

TABLE 1

Dependence of % Maximum Efficacy on X- and Y-Positions[a]

| Cmpd. # | X | Y | Affinity (nM) | Efficacy (% max)[c] |
|---|---|---|---|---|
| 1 | —NH— | NHC(O)CH$_3$ | 128 ± 5.97[e] | 5.18 ± 1.40[e] |
| 2 | —NH— | F | 7.96 ± 0.43[e] | 21.33 ± 2.22[e] |

It will be appreciated by a person skilled in the art that the present invention is not limited by what has been particularly shown and described hereinabove. Rather, the scope of the invention is defined by the claims that follow:

What is claimed is:

1. A method of binding an androgen receptor antagonist compound to an androgen receptor, comprising the step of contacting an androgen receptor compound of formula I:

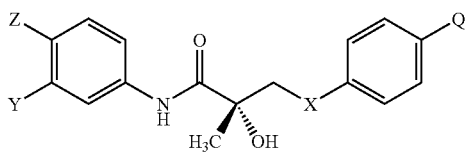

wherein
X is a NH, or NR;
Z is NO$_2$, CN, COOH, COR, or CONHR;
Y is CF$_3$, F, I, Br, Cl, CN or Sn(R)$_3$;
R is alkyl, haloalkyl, aryl, phenyl, halogen, alkenyl or OH; and
Q is alkyl, halogen, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR;
and/or its isomer, pharmaceutically acceptable salt, or any combination thereof, in an amount effective to bind the androgen receptor compound to the androgen receptor.

2. A method of suppressing spermatogenesis in a subject comprising contacting an androgen receptor of the subject with an androgen receptor compound of formula I:

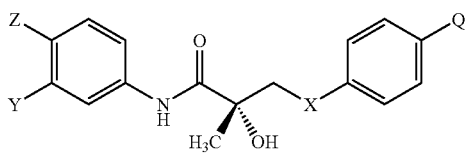

wherein
X is a NH, or NR;
Z is NO$_2$, CN, COOH, COR, or CONHR;
Y is CF$_3$, F, I, Br, Cl, CN or Sn(R)$_3$;
R is alkyl, haloalkyl, aryl, phenyl, halogen, alkenyl or OH; and
Q is alkyl, halogen, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR;
and/or its isomer, pharmaceutically acceptable salt, or any combination thereof, in an amount effective to suppress sperm production.

3. A method of hormone therapy comprising the step of contacting an androgen receptor of a subject with an androgen receptor compound of formula I:

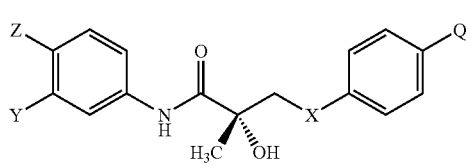

wherein
X is a NH or NR;
Z is NO$_2$, CN, COOH, COR, or CONHR;
Y is CF$_3$, F, I, Br, Cl, CN or Sn(R)$_3$;
R is alkyl, haloalkyl, aryl, phenyl, halogen, alkenyl or OH; and
Q is alkyl, halogen, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR;
and/or its isomer, pharmaceutically acceptable salt, or any combination thereof, in an amount effective to effect a change in an androgen-dependent condition.

4. A method of treating a subject having a hormone related condition, comprising the step of administering to said subject an androgen receptor compound of formula I:

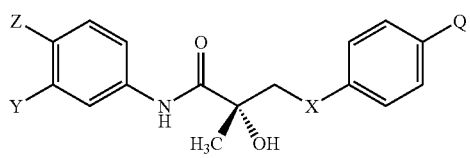

wherein
X is a NH, or NR;
Z is NO$_2$, CN, COOH, COR, or CONHR;
Y is CF$_3$, F, I, Br, Cl, CN or Sn(R)$_3$;
R is alkyl, haloalkyl, aryl, phenyl, halogen, alkenyl or OH; and
Q is alkyl, halogen, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR;
and/or its isomer, pharmaceutically acceptable salt, or any combination thereof, in an amount effective to effect a change in an androgen-dependent condition.

5. A method of treating a subject suffering from prostate cancer, comprising the step of administering to said subject an androgen receptor compound of formula I:

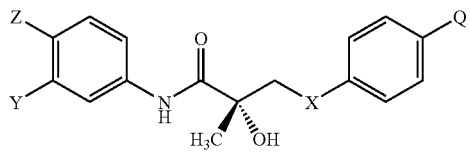

wherein
X is a NH, or NR;
Z is NO$_2$, CN, COOH, COR, or CONHR;
Y is CF$_3$, F, I, Br, Cl, CN or Sn(R)$_3$;

R is alkyl, haloalkyl, aryl, phenyl, halogen, alkenyl or OH; and

Q is alkyl, halogen, N(R)$_2$, NHCOCH$_3$, NHCOCF$_3$, NUCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR;

and/or its isomer, pharmaceutically acceptable salt, or any combination thereof, in an amount effective to treat prostate cancer in said subject.

6. A method of delaying the progression of prostate cancer in a subject suffering from prostate cancer, comprising the step of administering to said subject an androgen receptor compound of formula I:

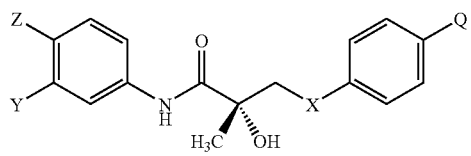

wherein

X is a NH, or NR;

Z is NO$_2$, CN, COOH, COR, or CONHR;

Y is CF$_3$, F, I, Br, Cl, CN or Sn(R)$_3$;

R is alkyl, haloalkyl, aryl, phenyl, halogen, alkenyl or OH; and

Q is alkyl, halogen, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR;

and/or its isomer, pharmaceutically acceptable salt, or any combination thereof, in an amount effective to delay the progression of prostate cancer in said subject.

7. A method of treating the recurrence of prostate cancer in a subject suffering from prostate cancer, comprising the step of administering to said subject an androgen receptor compound of formula I:

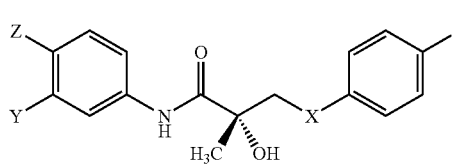

wherein

X is a NH, or NR;

Z is NO$_2$, CN, COOH, COR, or CONHR;

Y is CF$_3$, F, I, Br, Cl, CN or Sn(R)$_3$;

R is alkyl, haloalkyl, aryl, phenyl, halogen, alkenyl or OH; and

Q is alkyl, halogen, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R or SR;

and/or its isomer, pharmaceutically acceptable salt, or any combination thereof, in an amount effective to treat the recurrence of prostate cancer in said subject.

* * * * *